United States Patent
Hilmersson

Patent Number: 5,424,034
Date of Patent: Jun. 13, 1995

[54] METHOD AND AN APPARATUS FOR STERILIZING A CONTINUOUS PACKAGING MATERIAL WEB

[75] Inventor: Anders Hilmersson, Lund, Sweden

[73] Assignee: Tetra Laval Holdings & Finance SA, Pully, Switzerland

[21] Appl. No.: 115,787

[22] Filed: Sep. 3, 1993

Related U.S. Application Data

[63] Continuation of Ser. No. 913,054, Jul. 14, 1992, abandoned.

[30] Foreign Application Priority Data

Jul. 17, 1991 [SE] Sweden ................................. 9102190

[51] Int. Cl.⁶ .......................... A61L 2/06; A61L 2/20; B65B 55/06; F26B 3/04
[52] U.S. Cl. .......................... 422/28; 34/339; 34/350; 34/389; 34/414; 34/415; 34/426; 34/459; 34/503; 53/425; 422/31; 422/33; 422/293
[58] Field of Search ..................... 53/425, 426; 34/330, 34/337, 339, 343, 348, 350, 389, 414, 415, 426, 444, 446, 459, 503; 422/26-28, 31, 33, 38, 292, 293, 300, 306

[56] References Cited

U.S. PATENT DOCUMENTS

| | | | |
|---|---|---|---|
| 3,577,653 | 5/1971 | McClenathan et al. | 34/640 |
| 3,904,361 | 9/1975 | Egger | 422/27 |
| 3,947,249 | 3/1976 | Egger | 422/300 |
| 4,225,556 | 9/1980 | Löthman et al. | 53/425 X |
| 4,888,155 | 12/1989 | Posey et al. | 422/293 X |
| 5,022,167 | 6/1991 | Nakamura | 34/655 |
| 5,114,670 | 5/1992 | Duffey | 422/28 |
| 5,114,671 | 5/1992 | Olanders | 422/28 X |
| 5,178,841 | 1/1993 | Vokins et al. | 422/28 X |

FOREIGN PATENT DOCUMENTS

| | | |
|---|---|---|
| 0290139 | 11/1988 | European Pat. Off. |
| 0361858 | 4/1990 | European Pat. Off. |
| 459083 | 6/1989 | Sweden |
| 461264 | 1/1990 | Sweden |

Primary Examiner—Robert J. Warden
Assistant Examiner—L. M. Crawford
Attorney, Agent, or Firm—Burns, Doane, Swecker & Mathis

[57] ABSTRACT

The disclosure relates to a method and an apparatus for treating, for purposes of sterilization, a continuous material web (16) by bringing the entire web or parts thereof intended for sterilization into contact with liquefied hydrogen peroxide and thereafter drying the web with the aid of a hot gaseous fluid.

In order to improve the degree of destruction of microorganisms present on the material web, the material web is dried, after contact with the liquefied hydrogen peroxide, with air which has been intentionally supplied with hydrogen peroxide.

The apparatus for carrying out the method displays an elongate space (15) fitted with inlet (13) and outlet (11) for the material web, through which space the material web is disposed to be led, and an outer flow duct (17) disposed in communication with the inlet and the outlet and provided with means (18) for supplying hot hydrogen peroxide-free air for mixing with a portion of the hydrogen peroxide-containing air after the drying operation, and recycling of the mixed, hydrogen peroxide-containing air through the elongate space (15) in the direction of movement of the material web for a new drying cycle.

10 Claims, 2 Drawing Sheets

METHOD AND AN APPARATUS FOR STERILIZING A CONTINUOUS PACKAGING MATERIAL WEB

This application is a continuation of application Ser. No. 07/913,054, filed Jul. 14, 1992, now abandoned.

TECHNICAL FIELD

The present invention relates to a method of treating, for sterilization purposes, a continuously running material web, according to which method the whole of the web or parts thereof intended for sterilization are brought into contact with liquefied hydrogen peroxide and thereafter dried with the aid of a hot gaseous fluid.

The present invention also relates to an apparatus for treating, for sterilization purposes, a continuously running material web, the apparatus comprising a first treatment station including a device for bringing all of the web or parts thereof intended for sterilization into contact with liquefied hydrogen peroxide, and a second treatment station including a device for drying the material web with the aid of hot gaseous fluid.

BACKGROUND ART

In packaging technology, use is often made of so-called aseptic packaging techniques in order to impart longer shelf-life to and facilitate the distribution of foods and pharmaceuticals and other types of products which are particularly perishable and/or sensitive to bacterial attack. Fundamentally, the principle of the aseptic packaging technique is based on filling and sealing the product in packages which are ready for distribution, under sterile or bacteria-free conditions, in order to create the best possible circumstances for transporting and storing the product in the unopened package with retained freshness qualities during lengthy periods of time from the date of packaging and without any need for cold storage. In order that such a sterile or aseptic package be technically feasible, it is necessary that both the product which is to be packed and the material from which the package is produced are sterilized, and that the filling of the sterilized product into the package made from the sterilized packaging material be carried out under such conditions that the risk of reinfection of the product is eliminated entirely or to all intents and purposes.

A very large group of known aseptic packages for products of the type mentioned above are now most generally produced with the aid of modern, rational packaging machines of the type which, either from a web or from prefabricated blanks of a packaging material, both form, fill and seal the finished cartons or packages. Packages are produced from, for instance, a single web in that the web is first sterilized by being brought—entirely or in parts intended for sterilization—into contact with liquefied hydrogen peroxide in that the web is led down into and through a heated hydrogen peroxide bath. After passage through the hydrogen peroxide bath, the web is passed through the nip between two cooperating and co-rotating nip rollers or cylinders with whose aid any entrained surplus of hydrogen peroxide will be removed from the web and recycled to the hydrogen peroxide bath. Thereafter, the web is dried with the aid of a hot gaseous fluid, for example sterile air, which is blown towards one or both faces of the web in order to dispel any residual hydrogen peroxide. After the drying operation, the web is reformed into a tube by both longitudinal edges of the web being united with one another in a longitudinal overlap seam or joint. The tube is filled with the relevant product (previously heat-treated or otherwise sterilized) and is divided into closed, combined package units by repeated transverse sealings of the tube below the product level in the tube. The package units are separated from one another by transverse incisions in the transverse sealing zones and are given the desired geometric—normally parallelepipedic—final form by a final forming and sealing operation during which the double-walled triangular corner flaps of the cushion-shaped package units are folded in and sealed against the outside of adjacent package walls. In order to avoid reinfection of the sterilized product, both the sterilization of the packaging material and the package forming and filling operations are carried out in an environment screened-off from the unsterile surroundings of the package by hot sterile air operating at slight excess pressure in relation to the ambient pressure.

In the above-described manner, aseptic packages are produced which possess good mechanical strength and configurational stability and further display superior chemical and bacterial tightness properties which create every potential for readily being able to handle and store the product in an unbroken package, with retained or but insignificantly affected freshness qualities during lengthy periods of time from the date of packing.

SUMMARY OF THE INVENTION

However, according to the present invention, it has surprisingly proved that it is feasible to realize aseptic packages with further improved sterility properties and consequentially improved preconditions for being able to package and store products which are perishable and sensitive to bacterial attack, with retained or but insignificantly affected freshness qualities under guaranteed extended storage times after the packing date. One object of the present invention is, therefore, to suggest guidelines as to how such improved aseptic packages may simply be produced with the aid of existing or slightly modified or retrofitted conventional equipment.

The object according to the present invention will be attained in that a method of the type described by way of introduction has been given the characterizing feature that the gaseous fluid consists of hydrogen peroxide-containing air, i.e. air which has been intentionally supplied with hydrogen peroxide.

The present invention springs in essence from the per se known fact that bacteria die in a hot, hydrogen peroxide filled atmosphere, and practical experiments which have been conducted show that the extermination of bacteria (log red) can be increased by at least 1.5 to 2 units (BsA) by drying the web or those parts of the web intended for sterilization with hot hydrogen peroxide-containing air, instead of employing solely hot air as previously.

A further object of the present invention is to propose a simple apparatus with whose aid the method according to the present invention may readily be reduced into practice.

This object is attained by means of an apparatus of the type described by way of introduction which has been given the characterizing features as set forth in appended claim 6.

Further practical, advantageous embodiments of the apparatus according to the present invention have moreover been given the characterizing features as set forth in appended subclaims 7 to 11.

BRIEF DESCRIPTION OF THE DRAWING FIGURES

The present invention will now be described and explained in greater detail hereinbelow, with particular reference to the accompanying drawing figures, FIG. 1 is a schematic view of an apparatus in accordance with the present invention; and, FIG. 2 is a schematic view of the apparatus of FIG. 1 in which liquid hydrogen peroxide bath is used to wet a material web.

DETAILED DESCRIPTION OF THE PREFERRED EMBODIMENTS

Figure 1:
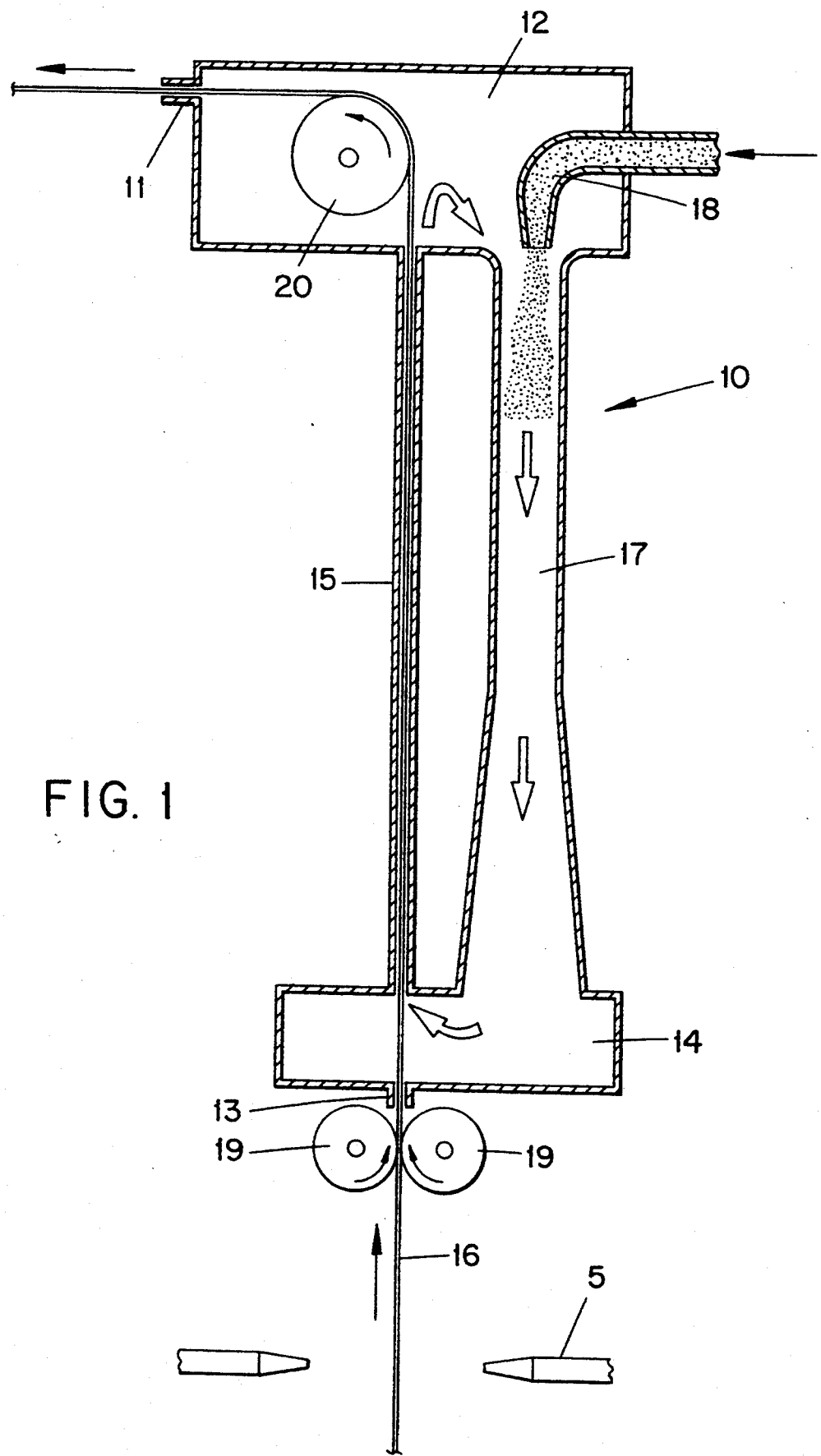

Referring to the drawing figures, the apparatus has been given the generic reference numeral 10. The apparatus 10 includes an outlet chamber 12 fitted with an outlet 11 and disposed at the upper region of the apparatus, and an inlet chamber 14 disposed at the lower region of the apparatus and fitted with an inlet 13. Both of the chambers 12 and 14 are in fluid communication with one another through an elongate space 15 extending substantially vertically between the chambers and through which a material web 16 is disposed to be led for contact with hydrogen peroxide-containing air which is simultaneously caused to flow through the elongate space 15 in the direction of movement of the material web for drying the web. The two chambers 12 and 14 are further interconnected with one another by the intermediary of an outer flow duct 17 extending between them for recycling at least a portion of the hydrogen peroxide-containing air flowing through the elongate space 15 from the outlet chamber 12 to the inlet chamber 14 for admixture of hot hydrogen peroxide-free air which is arranged to be supplied through an injector 18 discharging in the outlet chamber 12.

Ahead of the inlet 13 for the material web in the inlet chamber 14, there are disposed two co-rotating nip roller of nip cylinders 19 between which the material web 16 is disposed to be led for mechanical dispelling of liquefied hydrogen peroxide which has accompanied the material web 16 and with which the web, or pads thereof intended for sterilization, has been brought into contact for the destruction of bacteria.

Figure 2:
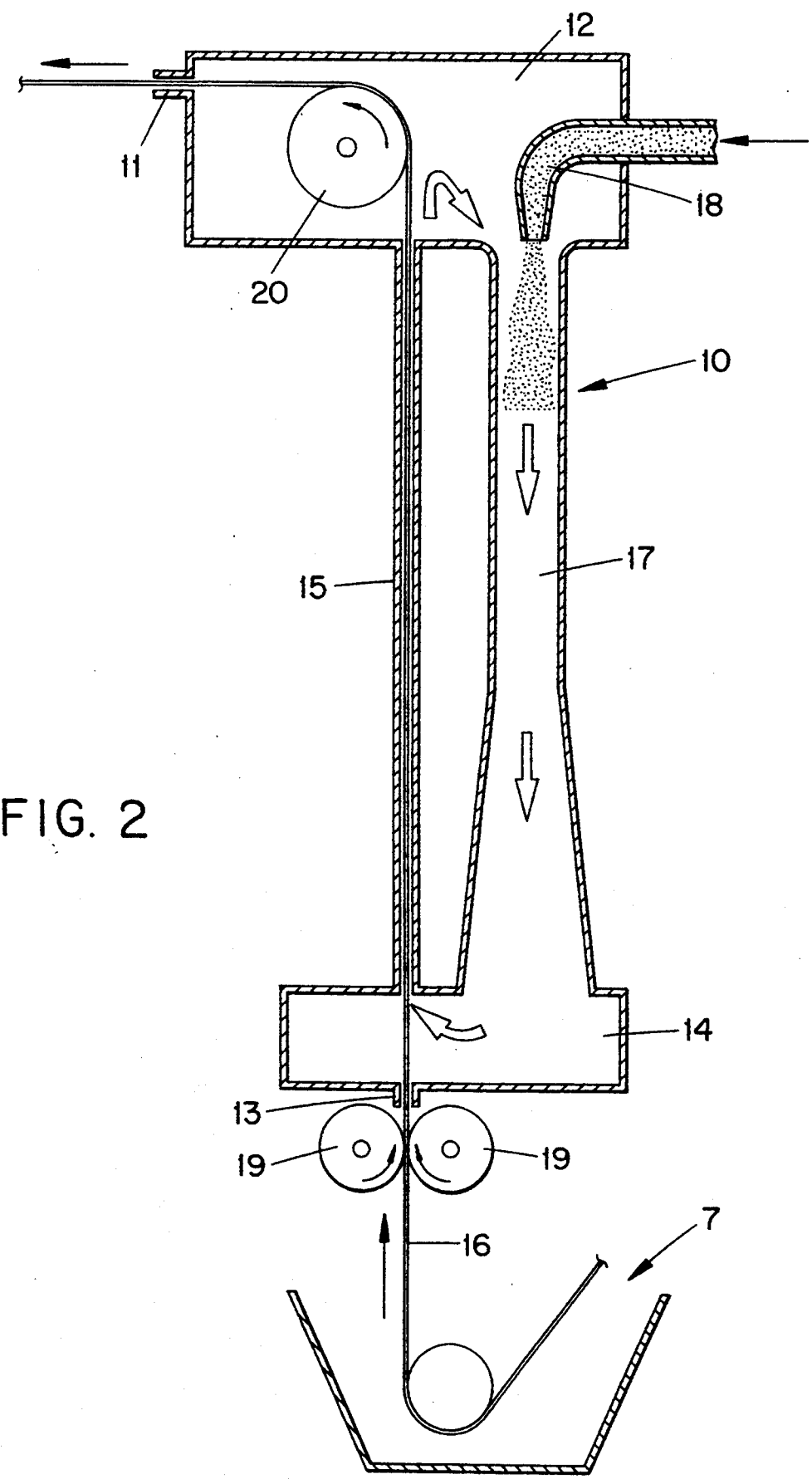

In a preceding treatment stations, shown schematically, the liquefied hydrogen peroxide serving as sterilization agent for the web can have been applied to the web or those pads thereof intended for sterilization, either with the aid of spray nozzles 5 directed towards one or both faces of the web, as shown in FIG. 1, or similar spray devices with whose aid the liquefied hydrogen peroxide is applied in spray-mist or finely-divided form to the web for the formation of a hydrogen peroxide film covering all or the above-mentioned pads of the web. Alternatively, as illustrated in FIG. 2, the liquefied hydrogen peroxide may have been applied to the web by means of a heated hydrogen peroxide bath 7 through which the web is led in the preceding treatment station.

At the upper region of the apparatus, there is disposed, in the outlet chamber 12, a co-rotating bending roller or conducting roller 20 about which the material web 16 is disposed to be led for deflection of the direction of movement of the material web such that the material web may pass freely throughout the entire apparatus from the inlet 13 to and out through the outlet 11 disposed at a right angle to the inlet 13.

In order to ensure good contact between the material web 16 and the hydrogen peroxide-containing air flowing through the elongate space 15, the elongate space 15 is preferably in the form of a narrow elongate gap whose dimensions substantially correspond to or but slightly exceed corresponding dimensions of the passing material web. Similarly, the outlet 11 and the inlet 13 are designed as narrow gap apertures dimensioned in accordance with the geometric dimensions of the material web and contributing to sealing off the apparatus from its outer, unsterile surroundings.

The apparatus 10 may be integral in or constitute a part of a conventional packaging machine of the type which, from the material web 16, both forms, fills and seals finished aseptic packages in the manner described in the foregoing, the apparatus 10 being placed in a so-called aseptic housing at the packaging machine, between the previously-mentioned station for applying liquefied hydrogen peroxide to the material web intended for sterilization and a tube-forming and product-filling station (not shown) of the packaging machine. While not being apparent from the drawing figures, it will be obvious to a person skilled in the art that the preceding hydrogen peroxide treatment station of the packaging machine and the subsequent tube-forming and product-filling station are, like the illustrated intermediate drying station, well-protected from the outer, unsterile ambient atmosphere of the packaging machine and are preferably housed in a common machine casing (not shown) substantially completely sealed-off from the surroundings so as to prevent the penetration of bacteria and the consequential risk of reinfection of the sterilized and dried material web 16.

According to the present invention, the procedure is as follows for treating, for sterilization purposes, a continuously running material web with the aid of the above-described apparatus 10. The material web 16 which has been treated with hydrogen peroxide and mechanically scraped (or 'doctored') by means of the nip rollers 19 is led via the inlet 13 into the inlet chamber 14 of the apparatus into and through the elongate space 15 which, at the same time, is supplied with hot hydrogen peroxide-containing air from the outer flow duct 17 for contact with the web for dispelling remaining hydrogen peroxide residue. In this instance, the material web is displaced at a speed of approx. 0.4 m/sec., while the hydrogen peroxide-containing air (which has, at the inlet chamber 14, a temperature of approx. 150° C. and a hydrogen peroxide concentration of approx. 10,000 ppm) flows through the elongate space 15 in the direction of movement of the material web at a speed of approx. 20 m/sec. From the elongate space 15, the dried material web 16 is led via the bending roller or conducting roller 20 into the outlet chamber 12 of the apparatus out through the outlet 11 together with a minor accompanying flow of hydrogen peroxide-enriched air (approx. 0.01 kg/sec.), while a major fraction of the hydrogen peroxide-enriched air (approx. 0.04 kg/sec.) after passage through the space 15 is recycled to the inlet chamber 14 via the outer flow duct 17 for new contact with the material web 16. In the outer flow duct 17, the thus recycled hydrogen peroxide-enriched air, which, after the drying of the material web in the elongate space 15, is at a temperature of approx. 80° C. in the outlet chamber 12, is mixed with hot (approx. 400° C.) hydrogen peroxide-free air which is continuously fed to the injector 18 discharging in the outlet chamber 12 at a speed of approx. 100 m/sec in a quantity corresponding to that air volume which accompanies the material web 16 out through the outlet 11, i.e. approx. 0.01 kg/sec, so as to adjust the hydrogen peroxide content and temperature of the recycled hydrogen peroxide-containing air flow at approx. 10,000 ppm and 150° C., respectively, at the inlet chamber 14 and prior to entry into the elongate space 15 for new drying of the material web 16.

In the manner described above, it has proved to be possible to increase the destruction of bacteria on the material web 16 by at least 1.5–2 units (log red in respect of BsA) and thereby correspondingly improve the preconditions for producing aseptic packages from the material web treated using the method according to the present invention, as compared with conventional techniques according to which the material web is dried using hot hydrogen peroxide-free or hydrogen peroxide-poor air.

It might finally be pointed out that the method according to the present invention, while having been described in the context of packaging material webs such as webs of plastic-coated paper, is not, naturally, restricted exclusively to this practical application but could just as well be employed on other types of material webs which, for purposes of sterilization, are brought into contact with liquefied hydrogen peroxide and thereafter dried for dispelling remaining hydrogen peroxide residue from the web.

The present invention should not be considered as restricted to that described above and shown in the drawing figures, many modifications being conceivable without departing from the spirit and scope of the appended claims.

What we claim and desire to secure by Letters Patent is:

1. A method of treating, for purposes of sterilization, a continuous material web, comprising:
   applying to all of a continuous material web or parts thereof intended for sterilization liquefied hydrogen peroxide;
   exposing the web in a single chamber to heated air containing gaseous hydrogen peroxide in an amount sufficient for sterilizing the web for simultaneous drying by the heated air and sterilizing by the gaseous hydrogen peroxide; and,
   recirculating a portion of the heated air containing hydrogen peroxide to the chamber with additional heated, hydrogen peroxide-free air.

2. The method as claimed in claim 1, wherein the heated hydrogen peroxide-free air is injected in a return flow duct in the flow direction of the recirculated air.

3. The method as claimed in claim 1, wherein the material web is, during the drying and sterilizing, led through an elongate space provided with an inlet and outlet, through which space the heated air containing hydrogen peroxide is blown in the direction of movement of the material web.

4. The method as claimed in claim 1, wherein the material web is led through a bath containing the liquified hydrogen peroxide, and that the web, after passage through the bath, is fed through a nip between two co-rotating nip rollers for removing accompanying surplus hydrogen peroxide prior to drying and sterilizing with heated air containing hydrogen peroxide.

5. A method of sterilizing a continuous material web, comprising:
   applying liquified hydrogen peroxide to a continuous material web;
   moving the web through an elongated chamber through which heated air containing hydrogen peroxide is flowing for simultaneously drying and sterilizing the web;
   allowing a first portion of the heated air to exhaust from the elongated chamber as the web exits the chamber;
   recirculating a second portion of the heated air containing hydrogen peroxide vapor through an outer flow duct to return to the elongated chamber, the second portion being larger than the first portion; and,
   injecting heated fresh air into the outer flow duct in the direction of flow for heating the recirculating second portion and maintaining the circulation through the elongated chamber,
   wherein recirculating the second portion of the heated air containing hydrogen peroxide vapor with injected heated air maintains the hydrogen peroxide vapor in an amount and at a temperature sufficient for sterilizing the web.

6. The method as claimed in claim 5, wherein the heated air containing hydrogen peroxide vapor is circulated in the elongated chamber in the direction of movement of the material web at a speed greater than the speed of the material web.

7. The method as claimed in claim 5, wherein the step of applying liquified hydrogen peroxide to the web is by leading the web through a bath containing liquified hydrogen peroxide, and after passage through the bath, feeding the web between two co-rotating nip rollers for removing accompanying surplus liquified hydrogen peroxide prior to entry into the drying and sterilizing chamber.

8. The method as claimed in claim 5, wherein the step of applying liquified hydrogen peroxide to the web is by spraying atomized liquified hydrogen peroxide on the web.

9. The method as claimed in claim 5, wherein the hydrogen peroxide vapor in the heated air is maintained at a concentration of about 10,000 parts per million of air.

10. The method as claimed in claim 5, wherein injecting the heated fresh air maintains the hydrogen peroxide vapor at about 150° C.

* * * * *